US011224431B2

(12) United States Patent
Imai et al.

(10) Patent No.: US 11,224,431 B2
(45) Date of Patent: Jan. 18, 2022

(54) LUMEN MAINTAINING CATHETER FOR SUTURING BLOOD VESSEL

(71) Applicant: MEDFORCE JAPAN CO., LTD., Utsunomiya (JP)

(72) Inventors: Takanori Imai, Utsunomiya (JP); Hiroshi Hirota, Utsunomiya (JP); Tomohiro Murakami, Utsunomiya (JP)

(73) Assignee: MEDFORCE JAPAN CO., LTD., Utsunomiya (JP)

( * ) Notice: Subject to any disclaimer, the term of this patent is extended or adjusted under 35 U.S.C. 154(b) by 0 days.

(21) Appl. No.: 16/625,867

(22) PCT Filed: Sep. 25, 2018

(86) PCT No.: PCT/JP2018/035332
§ 371 (c)(1),
(2) Date: Dec. 23, 2019

(87) PCT Pub. No.: WO2019/082573
PCT Pub. Date: May 2, 2019

(65) Prior Publication Data

US 2020/0121322 A1    Apr. 23, 2020

(30) Foreign Application Priority Data

Oct. 27, 2017 (JP) ............................ JP2017-207719

(51) Int. Cl.
*A61B 17/11* (2006.01)
*A61B 17/04* (2006.01)

(52) U.S. Cl.
CPC .......... *A61B 17/11* (2013.01); *A61B 17/0469* (2013.01); *A61B 2017/1103* (2013.01); *A61B 2017/1107* (2013.01)

(58) Field of Classification Search
CPC ................ A61B 17/11; A61B 17/0469; A61B 2017/1103; A61B 2017/1107;
(Continued)

(56) References Cited

U.S. PATENT DOCUMENTS 3,095,871 A * 7/1963 Mann ................ A61B 1/00082
600/435
4,959,067 A * 9/1990 Muller .................. A61B 17/00
600/201
(Continued)

FOREIGN PATENT DOCUMENTS

JP S60-36039 A 2/1985
JP H11-335 A 1/1999
(Continued)

OTHER PUBLICATIONS

Nov. 13, 2018 International Search Report issued in International Patent Application No. PCT/JP2018/035332.

*Primary Examiner* — Brooke Nicole Labranche
(74) *Attorney, Agent, or Firm* — Oliff PLC

(57) ABSTRACT

There is provided a lumen maintenance catheter used for vascular suture, in which an operator can stably grip the catheter to improve the operability, and the entire catheter is prevented from entering a blood vessel. The lumen maintenance catheter for vascular suture includes a shaft having flexibility and a bulging part bulging in a radial direction at a distal end of the shaft, wherein the shaft includes a small diameter part on a distal end side, and a large diameter part larger in diameter than the small diameter part, on a rear end side, the small diameter part and the large diameter part are connected by an inclined part that is inclined so that a diameter of the shaft increases toward the rear end side, and the rigidity of the shaft increases as the diameter increases.

5 Claims, 2 Drawing Sheets

(58) Field of Classification Search
CPC ... A61B 1/00082; A61B 5/035; A61B 5/1076; A61B 2017/320044; A61B 2017/320056; A61M 31/005
See application file for complete search history.

(56) References Cited

U.S. PATENT DOCUMENTS

| | | | |
|---|---|---|---|
| 6,319,193 B1 | 11/2001 | Arai et al. | |
| 6,626,872 B1 | 9/2003 | Navia et al. | |
| 2005/0234482 A1 | 10/2005 | Guenst | |
| 2016/0158529 A1* | 6/2016 | Thompson-Nauman | A61N 1/05 606/129 |

FOREIGN PATENT DOCUMENTS

| | | |
|---|---|---|
| JP | 5937729 B1 | 6/2016 |
| WO | 92/019161 A1 | 11/1992 |
| WO | 99/063895 A1 | 12/1999 |
| WO | 2002/022197 A2 | 3/2002 |

* cited by examiner (A)

(B)

(C)

LUMEN MAINTAINING CATHETER FOR SUTURING BLOOD VESSEL

TECHNICAL FIELD

This application relates to the technical field of lumen maintenance catheters used for suturing blood vessels.

BACKGROUND in an anastomosis operation and the like, in which a blood vessel is connected to another blood vessel, a suture of blood vessel walls is performed. In general, blood vessels are sutured by an operation of suturing one side surface of the blood vessel wall with a suture needle and a suture thread. When a blood flow is stopped during treatment, a vascular lumen may be crushed, the blood vessel may become flat, and the inner surfaces of the blood vessel walls facing each other may come close to each other. If suturing is performed in such a case, there is a risk that a suture needle may reach not only the surface of the blood vessel wall on the side to be sutured, but also the surface of the blood vessel wall on the opposite side, and the surface on the opposite side may be sutured together.

As a medical device for solving such a problem, a lumen maintenance catheter for vascular suture including a bulging part bulging outside in a radial direction at a distal end part of a shaft having flexibility is known (see, for example, Patent Literature 1 and Non-Patent Literature 1). When such a lumen maintenance catheter is inserted into a lumen of a blood vessel, a vascular lumen in the vicinity of a suture site is maintained by the bulging part at the distal end without being crushed. Thus, it is possible to prevent the surface on the opposite side from being sutured together during suturing. Further, such a lumen maintenance catheter for vascular suture can be used for other purposes such as measurement of the inner diameter of a blood vessel and check for the presence or absence and the position of vascular stenosis.

CITATION LIST

Patent Literature

Patent Literature 1: Japanese Patent No. 5937729

Non-Patent Literature

Non-Patent Literature 1: Document Attached to Medical Device, provided by the Incorporated administrative agency, Pharmaceuticals and Medical Devices Agency, Approval Number 20400BZY00147000

SUMMARY

Technical Problem

However, the shaft of each of the lumen maintenance catheters for vascular suture described in Patent Literature 1 and Non-Patent Literature 1 has a cylindrical shape having the same diameter from the distal end to the rear end, and the rigidity of the shaft is almost same from the distal end to the rear end. During vascular suturing, the distal end side of the shall inserted into the blood vessel is operated by gripping and operating the rear end side of the shaft. However, if the shaft is formed with the same diameter and has the same rigidity, there is a problem in that it is difficult to achieve stable operation. The reason for this is that, since the gripping part has a small diameter, delicate operation is difficult, and since the rigidity is the same, the shaft deforms from the vicinity of the gripped position. Further, in a case of checking for vascular stenosis, if a lumen maintenance catheter for suturing is used for a relatively long blood vessel, there is a risk that the entire catheter will accidentally enter the blood vessel if there is no stenosis.

Accordingly, there is a need for providing a lumen maintenance catheter for vascular suture capable of being stably operated and being prevented from entirely entering a blood vessel.

Solution to Problem

The disclosed embodiments have been contrived in view of the above circumstances, and an object of the disclosed embodiments is to solve the above problems. In one embodiment, there is provided a lumen maintenance catheter for vascular suture including a shaft having flexibility and a bulging part bulging in a radial direction at a distal end of the shaft, wherein the shaft includes a small diameter part on a distal end side and a large diameter part larger in diameter than the small diameter part, on a rear end side, the small diameter part and the large diameter part are connected by an inclined part that is inclined so that a diameter of the shaft increases toward the rear end side, and the rigidity of the shaft increases as the diameter increases.

In the lumen maintenance catheter for vascular suture, half or more of a total length of the shaft may be occupied by the small diameter part.

Advantageous Effects

In embodiments, the large diameter part acts as a stable gripping part during vascular suturing, and due to a difference in rigidity between the large diameter part and the small diameter part, a position where the shaft deforms is stabilized, and thus, the operability is improved. Further, in a case of checking for vascular stenosis, since the shaft includes the large diameter part, it is possible to prevent the entire lumen maintenance catheter from entering the blood vessel. Further, since the lumen maintenance catheter includes the inclined part connecting the large diameter part and the small diameter part, no level difference is formed between the large diameter part and the small diameter part, and thus, the risk of inadvertently damaging the blood vessel during insertion of the catheter into the blood vessel can be reduced, and an operator can smoothly operate the catheter without feeling a hitch between level differences even if the operator operates the catheter while appropriately adjusting a position gripped by the operator.

In embodiments, the front half portion of the shaft may have a small diameter, and thus, the distal end side of the shaft can be operated flexibly.

BRIEF DESCRIPTION OF THE DRAWINGS

FIG. 213 is an enlarged view along cross-section A-A in 1B.

DETAILED DESCRIPTION

Figure 1:
FIG. 1A is a plan view.
FIG. 1B is a front view.
FIG. 1C is a bottom view of a lumen maintenance catheter for vascular suture according to embodiments.
Figure 1:
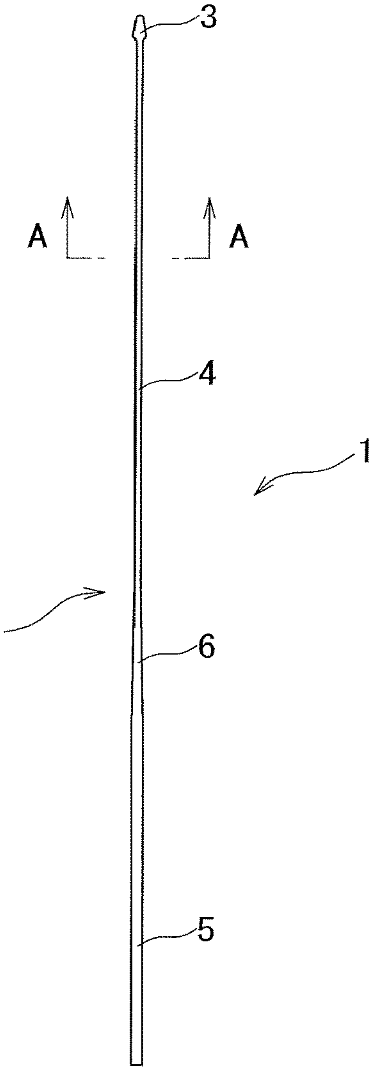
Figure 1:
Figure 2:
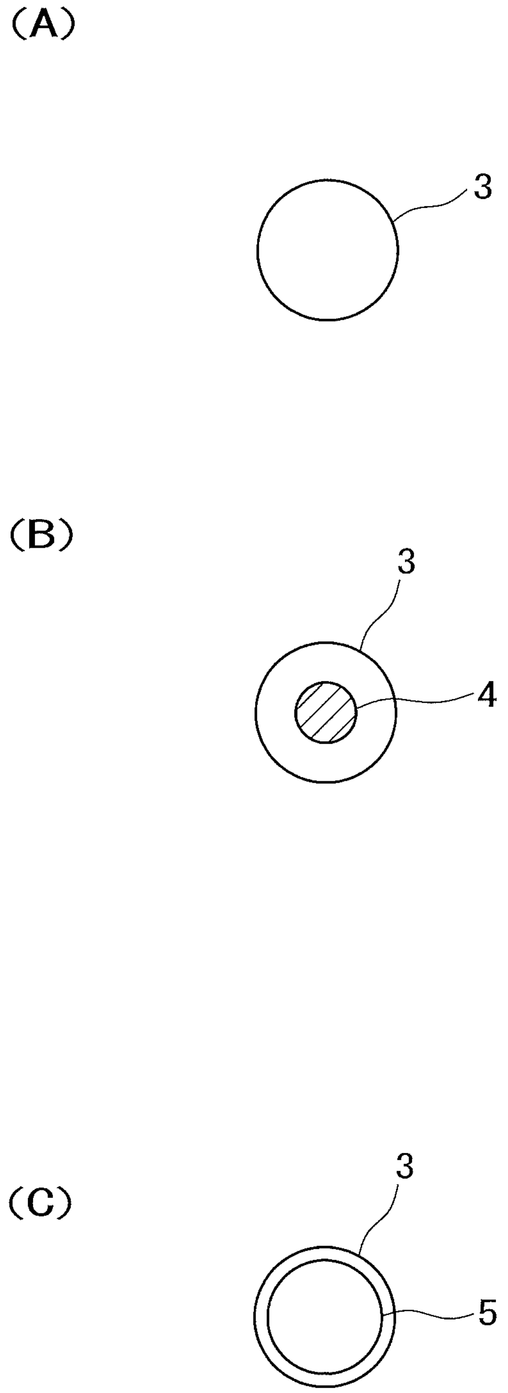
FIG. 2A is an enlarged view of FIG. 1A.
FIG. 2C is an enlarged view of FIG. 1C.

Below, embodiments will now be described with reference to the drawings. In the drawings, reference numeral 1 denotes a lumen maintenance catheter for vascular suture (which may simply be referred to as "catheter" hereinafter) including a long shaft 2 having flexibility and a bulging part 3 formed at a distal end of the shaft 2 and bulging in a radial direction. The shaft 2 includes a small diameter part 4 on the distal end side and a large diameter part 5 on the rear end side, and the small diameter part 4 and the large diameter part 5 are connected by an inclined part 6 that is continuously inclined so that a diameter of the shaft 2 increases toward the rear end side. In FIG. 1B, a front view of the catheter 1 is illustrated, however, the left and right side views and the rear view are each the same as the front view.

The shaft 2 is made of a flexible material and is solid. More specifically, the material is preferably a synthetic resin such as a fluororesin, polyurethane, or polypropylene. Further, the outer peripheral surface of the shaft 2 may be coated to form a multilayer. The total length of the shaft 2 is about 150 mm. However, the length of the shaft 2, including the lengths of the below-described small diameter part 4 and large diameter part 5, can be set appropriately.

The bulging part 3 is a portion to be inserted first into a blood vessel, as a distal end part of the catheter 1. The bulging part 3 bulges in the radial direction of the shaft 2, and has a teardrop shape in a front view and a circular shape in a plan view. For example, the bulging part 3 may be injection-molded, etc., together with the shaft 2 or may be coupled to the shaft 2 as a separate member. The material of the bulging part 3 may be the same material as the shaft 2 or may be a different material from the shaft 2. Further, the shape of the bulging part 3 is not limited to the teardrop shape, and may be a spherical shape or may be a hook shape bulging only in any one direction of the radial direction. However, considering that the bulging part 3 is to be inserted into a blood vessel, it is preferable that the bulging part 3 has a shape that does not damage the blood vessel.

The bulging part 3 functions as a support for the blood vessel so that, when the bulging part 3 is disposed in the lumen in the vicinity of the anastomosis site during vascular anastomosis, it is possible to suture only one wall surface part of the blood vessel. Further, in a case of checking for vascular stenosis, the bulging part 3 functions to abut against the stenosis part to create resistance against the insertion of the catheter 1 or to prevent further insertion of the catheter 1. Therefore, as long as these functions can be exhibited, the bulging part 3 may have an appropriate shape. However, it is preferable that the shape of the bulging part 3 allows for smooth insertion and removal of the catheter 1.

The small diameter part 4 occupies about 80 mm on the distal end side of the shaft 2, and has a diameter of about 0.8 mm. On the other hand, the large diameter part 5 occupies about 50 mm on the rear end side of the shaft 2, and has a diameter of about 1.5 mm. The inclined part 6 is formed in a tapered shape over about 20 mm between the small diameter part 4 and the large diameter part 5. The small diameter part 4, the large diameter part 5, and the inclined part 6 are each formed coaxially in a circular shape in cross section, and in the present embodiment, are manufactured by injection-molding the same material. In the shaft 2, since the small diameter part 4, the large diameter part 5, and the inclined part 6 are all made of the same material and solid, the small diameter part 4 has the lowest rigidity, the rigidity gradually increases from the small diameter part 4 to the inclined part 6, and the large diameter part 5 has the highest rigidity. Therefore, the large diameter part 5 mainly functioning as a gripping part and not being inserted into the blood vessel, is higher in rigidity than the small diameter part 4, so that an operator can stably operate the catheter 1 when operating the distal end side of the catheter 1. It is noted that each of the parts should not be always solid. However, the large diameter part 5 should have a rigidity higher at least than the small diameter part 4.

The length of each of the small diameter part 4, the large diameter part 6, and the inclined part 5, and the ratio of each of the small diameter part 4, the large diameter part 6, and the inclined part 5 with respect to the total length of the shaft 2 can be set appropriately. The small diameter part 4 preferably occupies half or more of the total length of the shaft 2, at least on the front end side of the shaft 2.

The inclined part 6 may be linearly inclined. The inclined part 6 may also be chamfered at a portion connecting the small diameter part 4 and the large diameter part 5, or may be provided with an appropriate gradient for the inclination.

According to an improved modification of the present embodiment, the shaft includes an appropriate scale, and thus, the amount of insertion into the blood vessel can be easily made visually recognizable. Further, the catheter 1, including each part, may not necessarily have a circular shape in a plan view, and may have an elliptical shape or an oval shape, for example.

According to the embodiments configured as described, in the lumen maintenance catheter for vascular suture 1, the shaft 2 having flexibility includes the small diameter part 4 on a distal end side, and the large diameter part 5 larger in diameter than the small diameter part 4, on a rear end side, and the small diameter part 4 and the large diameter part 5 are connected by the inclined part 6 that is inclined so that a diameter of the shaft increases toward the rear end side. Since the rigidity of the shaft 2 increases as the diameter increases, the small diameter part 4 on the distal end side of the shaft 2 has low rigidity, and is easily deformed to a desired shape, whereas the large diameter part 5 on the rear end side of the shaft 2 is a highly rigid and stable gripping part. A difference in rigidity between the small diameter part 4 and the large diameter part 5 stabilizes the position at which the shaft 2 is deformed, and thus, the operability is improved. Further, since the inclined part 6 is provided, there is no level difference even though the small diameter part 4 and the large diameter part 5 are provided, and thus, the risk of inadvertently damaging the blood vessel is reduced, and an operator can smoothly operate the catheter 1 without feeling a hitch between level differences.

Since the front half portion of the shaft 2 is occupied by the small diameter part 4, the front end portion can be operated flexibly.

It is noted that the disclosed embodiments are not limited to the specific embodiments described herein, and in particular, not to the specific disclosed numerical values and ratios. Further, in the present embodiment and claims, the catheter is referred to as being used "for vascular suture," however, this obviously does not exclude the embodiments from being used in vascular anastomosis.

INDUSTRIAL APPLICABILITY

The disclosed embodiments can be utilized for a lumen maintenance catheter for vascular suture in which a shape of a vascular lumen is maintained during suturing a blood vessel.

The invention claimed is:

1. A lumen maintenance catheter for vascular suture, the catheter comprising: an integrally formed solid shaft having flexibility, the shaft being formed by injection-molding a same material; and a bulging part disposed at a distal end of the shaft and bulging in a radial direction of the shaft, wherein the shaft includes a small diameter portion on a distal end side, a large diameter portion on a rear end side, and an inclined portion disposed between the small diameter portion and the large diameter portion, the large diameter portion is larger in diameter than the small diameter portion, the small diameter portion and the large diameter portion are connected by the inclined portion which is continuously inclined so that a diameter of the shaft increases toward the rear end side, a rigidity of the shaft increases as the diameter of the shaft increases, half or more of a total length of the shaft is occupied by the small diameter portion, the small diameter portion has a constant diameter, and the large diameter portion has a constant diameter, the large diameter portion having a length that is longer than a length of the bulging part so as to enable the lumen maintenance catheter to be operated by gripping the large diameter portion.

2. The lumen maintenance catheter for vascular suture according to claim 1, wherein the small diameter portion, the inclined portion and the large diameter portion are each formed coaxially.

3. The lumen maintenance catheter for vascular suture according to claim 1, wherein the inclined portion is linearly inclined.

4. The lumen maintenance catheter for vascular suture according to claim 1, wherein, in the inclined portion, the diameter of the shaft gradually increases toward the rear end side.

5. The lumen maintenance catheter for vascular suture according to claim 1, wherein, in the inclined portion, the diameter of the shaft continuously increases toward the rear end side.

* * * * *